(12) United States Patent
Wu

(10) Patent No.: US 8,420,135 B2
(45) Date of Patent: Apr. 16, 2013

(54) USE OF COCONUT WATER EXTRACT OR COCONUT SHELL EXTRACT FOR TREATING IMMUNOLOGICAL DISEASES AND/OR DISORDERS

(76) Inventor: Rong-Tsun Wu, Taipei (TW)

( * ) Notice: Subject to any disclaimer, the term of this patent is extended or adjusted under 35 U.S.C. 154(b) by 0 days.

(21) Appl. No.: 12/954,185

(22) Filed: Nov. 24, 2010

(65) Prior Publication Data

US 2011/0123648 A1    May 26, 2011

Related U.S. Application Data

(60) Provisional application No. 61/264,254, filed on Nov. 25, 2009.

(51) Int. Cl.
| | |
|---|---|
| *A01N 65/00* | (2009.01) |
| *A61K 38/00* | (2006.01) |
| *A61K 36/00* | (2006.01) |
| *A61P 19/02* | (2006.01) |
| *A61P 29/00* | (2006.01) |

(52) U.S. Cl.
USPC .......... 424/727; 514/16.6; 514/825; 424/769; 424/776

(58) Field of Classification Search ........................ None
See application file for complete search history.

(56) References Cited

PUBLICATIONS

Kirszberg et al. (2003) Phytother. Res. 17, pp. 1054-1058.*
Herath et al. (2003) J. Med. Food 6 (4) pp. 365-370.*
Alviano et al. (2004) J. Ethnopharm. 92 pp. 269-273.*
Esquenazi et al. (2002) Research in Microbiology 153 pp. 647-652.*
Bharrhan et al., "Catechin Suppresses an Array of Signalling Molecules and Modulates Alcohol-Induced Endotoxin Mediated Liver Injury in a Rat Model," PLoS ONE, 6: e20635, 9 pages (2011).
Chang et al., "Quantification of (+)-catechin and (−)-epicatechin in coconut water by LC-MS," Food Chemistry 126:710-717 (2011).

* cited by examiner

*Primary Examiner* — Chris R Tate
*Assistant Examiner* — Russell Fiebig
(74) *Attorney, Agent, or Firm* — Edwards Wildman Palmer LLP; Peter F. Corless

(57) ABSTRACT

A method for treating immunological diseases and/or disorders associated with tumor necrosis factor-alpha (TNF-α) in a subject in need thereof is disclosed. The method comprises administering to a subject in need thereof a therapeutically effective amount of the coconut (*Cocos nucifera* Linn.) water extract or coconut (*Cocos nucifera* Linn.) shell extract through induction of transforming growth factor beta (TGF-β) or interleukin-10 (IL-10) as endogenous immunosuppressive factors.

9 Claims, 9 Drawing Sheets

USE OF COCONUT WATER EXTRACT OR COCONUT SHELL EXTRACT FOR TREATING IMMUNOLOGICAL DISEASES AND/OR DISORDERS

CROSS-REFERENCE TO RELATED PATENT APPLICATION

This application claims priority to provisional application No. 61/264,254 filed Nov. 25, 2009, which is incorporated herein by reference in its entirety.

FIELD OF THE INVENTION

The present invention relates generally to coconut water or coconut shell extract, and more specifically for treating immunological diseases and/or disorders.

BACKGROUND OF THE INVENTION

Coconut is used as tropical fruit and drink in the tropics. The antimicrobial and antiviral activity of husk fiber from coconut was reported to mainly due to the high content of phenolic compounds (Esquenazi D. et al. 2002.).

The bioactivities of coconut also included inhibitory activity against acyclovir-resistant herpes simplex virus type 1, leishmanicidal effects (Mendonça-Filho R R. et al. 2004.), protection of hemoglobin from nitrite-induced oxidation to methemoglobin (Mantena S K. et al. 2003.), and free radical scavenging activities (Alviano D S. et al. 2004.). Coconut water is the solution of coconut fruit as well as a common and natural refreshing drink with fewer side-effects reported. Coconut water is commonly used for nutritional formulation beverages and food products due to the presence of carbohydrates, vitamins, electrolytes, minerals and proteins (Santoso U. et al. 1996. and Campbell-Falck D. et al. 2000.). Besides, coconut water is also used for preservation of ovine ovarian follicles and dog semen, in vitro culture of goat primordial follicles (Figueiredo J. R. 2000. and Andrade E R. et al. 2002.), and plant tissue culture (Tiainen, T. 1993.). In addition, coconut water is reported to have inhibitory activity against human bacterial pathogens (Mandal S M. et al. 2009.) and antiulcerogenic effects (Nneli R O. and Woyike O A. 2008.).

In mammals, the skin is the largest organ of the integumentary system and plays a defensive barrier of the external pathogenic invasion. Skin inflammation has evolved as a protective response to injury, thus eliminates foreign organisms or material, and the resolution of inflammation protect us against excessive tissue injury. A failure of resolution cause chronic inflammatior, and lead to many skin diseases. In murine disease models has indicated heterogeneity of TNF receptor usage in autoimmune disease suppression versus inflammatory tissue damage, suggesting that selective TNF receptor inhibition may be advantageous to anti-TNF treatments in combating chronic inflammatory disease. (Apostolaki M, Armaka M, Victoratos P et al. 2010.) Tumour necrosis factor-alpha (TNF-α) levels in suction blister fluids and sera of psoriatic patients are correlated increases and have relationships with disease severity. (Ettehadi P. et al. 1994., Bonifati C. et al. 1994., Groves R. et al. 2004.)

Inflammation has evolved as a protective response to insult or injury, it's a primordial response that eliminates or neutralises foreign organisms or material, the resolution of inflammation encompasses the endogenous anti-inflammatory mechanisms that protect us against excessive tissue injury and promote the restoration of tissue structure and function. In fact, our well being and survival depends upon its efficiency and carefully-balanced control. In general, the innate inflammatory response initiates within minutes and, if all is well, resolves within hours. In contrast, chronic inflammation persists for weeks, months or even years. (Lawrence T. and Gilroy D. W. 2007.) In the late phase of acute inflammation, IL-10 and TGF-β will be produced to limit inflammation and promote resolution. These two cytokines (IL-10 and TGF-β) are associated with resolution of inflammation. (Lawrence T. and Gilroy D. W. 2007, Serhan C. N. et al. 2007.)

The liver plays an important role in immunological tolerance due to its anatomical location, as it links the gastrointestinal tract and the systemic venous circulation. Therefore, immune reactions against dietary or bacterial antigens from the gut have to be avoided. The function of the liver as clearance organ, however, harbors the danger that the substances that should be degraded and/or eliminated lead to tissue damage. Thus, effective defense mechanisms are necessary. Among the nonparenchymal cells Kupffer cells, sinusoidal endothelial cells, and natural killer (NK) lymphocytes exert cellular defense functions for the whole body but also for the liver itself. Furthermore, each cell type of the liver, including the hepatocytes, possesses its own defense apparatus. (Erhardt A. et al. 2010, Ramadori G. et. al. 2008.)

Rheumatoid arthritis pathology consists that synovial inflammation inside the joint capsule gives rise to a pannus, and then the pannus gradually invades the cartilage and even the surface of the bone. The immune system of patients with rheumatoid arthritis lost the ability to discriminate self from non-self. The immune system attacks synovial tissue and connective tissue in the highly movable joints of the limbs in the beginning, followed by disruption of the balance between bone formation and resorption, activating osteoclasts, and thus resulting in the destroy of articular cartilage and bone.

Because of the immunological mechanisms of rheumatoid arthritis involved in complex networks connecting a multitude of cells and cytokines, the detailed pathogenic mechanisms in rheumatoid arthritis remains unclear (Gary S. and Firestein, M. 2005.).

Pharmacologic treatments of rheumatoid arthritis and also other arthritis associated diseases, such as osteoarthritis, ankylosing spondylitis, and acute gouty arthritis, include non-steroidal anti-inflammatory drugs (NSAIDs), corticosteroids, disease modifying anti-rheumatic drugs (DMARDs), and biological agents. Because arthritis is an inflammatory condition, first-line therapy is aimed to suppress inflammation and to release symptoms, such as NSAIDs and corticosteroids, which are effective in controlling the pain, swelling and stiffness related to arthritis. However, these two treatments have adverse effects and limited impact on long-term outcomes. Biological agents, such as etanercept, infliximab, and adalimumab, are often combined used with methotrexate and have also been shown to be effective in rheumatoid arthritis patients but may be considered second choice because of cost consideration. DMARDs, including methotrexate, hydroxychloroquine, sulfasalazine, leflunomide, and other antirheumatic drugs, such as gold salts and cyclosporin, are slow-acting compounds and act mainly to inhibit the proliferation of immune cells as well as to diminish the inflammation. Although DMARDs are common used for diagnosed cases of rheumatoid arthritis, reported adverse reactions and toxicities should be concerned (Gaffo A. et al. 2006., Gary S. and Firestein, M. 2003., and Gary S. and Firestein, M. 2005.).

The complexity and redundancy of the regulatory mechanisms combined with the observed interpatient variability in the disease process explains why some patients may respond to a particular therapy whereas others do not, especially when targeting pathways downstream of key regulators of immunologic events. Current drugs specifically target upstream cytokines involved in the inflammatory response of rheumatoid arthritis, include the IL-1 inhibitors (e.g. anakinra and kineret), anti-tumor necrosis factor (anti-TNF-α) agents (e.g. etanercept, infliximab, and adalimumab), the co-stimulation blocker of T cell activation (e.g. abatacept), and the selective B cell depletion agent, for example, anti-CD20 monoclonal antibody (e.g. rituximab) (Gaffo A. et al. 2006., Gary S. and Firestein, M. 2003, and Gary S. and Firestein, M. 2005.). These agents can specifically inhibit abnormal immune response thus suppress the inflammation, however, patients are also at higher risk for infection because of the immunosuppressive side-effect.

Therefore, a heretofore unaddressed need exists in the art to address the aforementioned deficiencies and inadequacies, especially in connection with coconut water extract and coconut shell extract.

SUMMARY OF THE INVENTION

In one aspect, the invention relates to a method for treating immunological diseases and/or disorders associated with tumor necrosis factor-alpha (TNF-α) in a subject in need thereof, comprising administering a therapeutically effective amount of a coconut (*Cocos nucifera* Linn.) water extract or a coconut (*Cocos nucifera* Linn) shell extract through induction of transforming growth factor beta (TGF-β) or interleukin-10 (IL-10) as an endogenous immunosuppressive factor.

The coconut (*Cocos nucifera* Linn.) water extract or the coconut (*Cocos nucifera* Linn.) shell extract is prepared by a process comprising:
(a) passing coconut water or coconut shell water through a resin absorption chromatographic column, wherein the coconut shell water is obtained by adding water to coconut shell;
(b) washing out the column with water; and
(c) eluting the column by any combination of solutions or solvents capable of desorbing the coconut water extract or the coconut shell extract from the column.

The coconut (*Cocos nucifera* Linn) water extract or coconut (*Cocos nucifera* Linn.) shell extract is effective in treating the immunological diseases and/or disorders are at least one selected from the group consisting of skin inflammation, liver inflammation, and rheumatoid arthritis.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIG. 5F to 5J are 400. Ear skin biopsies collected at 36 h after topical TPA (80 μM) treatment. Two days pretreatment with different doses of coconut water extract (0.2, 1, 5 mg/kg/day) orally can suppress the induction of skin edema and reduce the inflammatory cell infiltration after TPA treatment.

DETAILED DESCRIPTION OF THE INVENTION

Definitions

Figure 1:
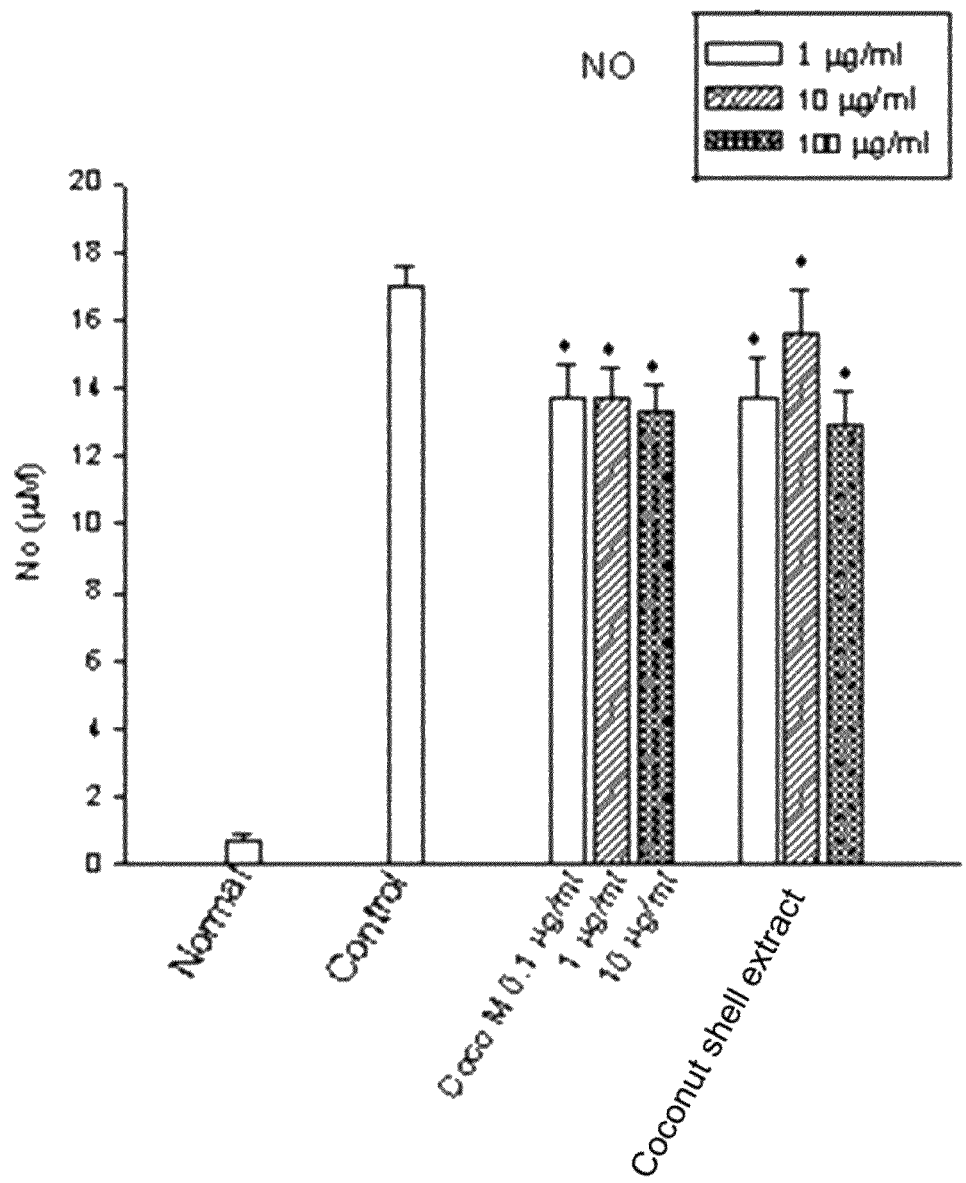
FIG. 1 is a diagram showing the effect of coconut water extract or coconut shell extract on LPS-induced inflammation of RAW 264.7 cells. The control group is RAW 264.7 cells administered with lipopolysaccharide (LPS) to induce inflammation. The treatment groups are administered with LPS in the presence of 0.1, 1 and 10 μg/ml coconut water extract or 1, 10 and 100 μg/ml coconut shell extract. The normal group is treated with neither LPS nor coconut water extract or coconut shell extract. Nitric oxide (NO) production, the inflammation marker, is measured by DAN assay. Results are expressed as means±S.D. (n=6). * indicates $p<0.05$.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

Preparation of Coconut Water Extract or Coconut Shell Extract

Coconut water and coconut shell of *Cocos nucifora* Linn. are obtained from 247.68 kg (for coconut water) and 2.1 kg (for coconut shell) fresh coconut fruits, (Pingtung Hsien, Taiwan) purchased from a fruiter. Add water to coconut shell and then break up with blender to get coconut shell water. Coconut water (47.6 L) or coconut shell water (2.7 L) is filtered by glass microfiber filters and the filtrate is chromatographed by consecutive passage through one Diaion HP-20 (Mitsubishi Chemical Co., Japan) (52 cm×5 cm) column at 4° C. The residual absorbed on the gel are first eluted with deionized water (4 L, flow rate: 20 ml/min) and then eluted by 100% methanol (ACS grade; Echo Chemical Co Ltd., Taiwan) (about 6.5 L, flow rate: 8.3 ml/min) at 4° C. until the $UV_{200-400\ nm}$ absorption signal of each eluate is undetectable. Each deionized water eluate is collected and lyophilized to gain the water eluate product which is mainly carbohydrates weighted 2438.9 g (for coconut water extract) or 130 g (for coconut shell extract). Each 100% methanol eluate is collected, concentrated by vacuum evaporation, and lyophilized to gain the methanol eluate product, named coconut water extract or coconut shell extract followed in this specification.

Chromatography by thin layer chromatography (TLC) is used to characterize the carbohydrate contents present in the deionized water and the ethanol eluates. TLC chromatograms are run on the silica TLC slide (Merck, Germany), using 1-butanol:acetic acid:water [3.2:4:0.6 (v/v)] as eluent, and polyamide TLC slide (Macherey-Nagel, Germany), using ethyl:pyridine:water [6:3:2 (v/v)] as eluate. Retention factor ($R_f$) value of the deionized water and 100% ethanol eluates are compared with carbohydrate standards (D(+)galactose, D(+)glucose, D(+)mannose, D(−)arabinose, D(−)ribose, D(+)xylose, and maltose; Sigma, USA) while all carbonhydrates are revealed by anisidine phthalate (Sigma, USA) reagent.

The $R_f$ value and the yielded color of the deionized water eluate are both closed to glucose and mannose standards, and it might suggest that glucose and mannose are the major monosaccharides in the coconut water or coconut shell. The result of 100% methanol eluate shows that there is almost no carbohydrate present in it.

Example 2

Effect of Coconut Water Extract or Coconut Shell Extract on Lipopolysaccharide-Induced Inflammation of RAW 264.7 Cells RAW 264.7 is a murine macrophage cell line and often used for study on inflammation. RAW 264.7 cells ($4 \times 10^4$ cells/well) are plated in DMEM high glucose (Gibco) containing 10% (v/v) fetal bovine serum (FBS; Gibco) on 96-well plate (Falcon) overnight and then treated with 1

μg/ml lipopolysaccharide (LPS; Sigma, USA) in the absence (control group) or presence of 0.1, 1 and 10 μg/ml coconut water extract or 1, 10 and 100 μg/ml coconut shell water extract. The normal group is treated with neither LPS nor coconut water extract or coconut shell extract. After a 24-h incubation period, supernatants are analyzed for nitric oxide (NO) production by DAN assay while cell viability is examined by resazurin assay.

NO participates in inflammation and thus can be used as a marker to evaluate the effect on the inflammation. 2,3-Diaminonaphthalene (DAN; Sigma, USA) is reduced with nitrate under acidic conditions to form 1-(H)-naphthotriazole, a fluorescent product. 100 μl of sample is first brought to plate. 50 μl of freshly prepared DAN (0.01 mg/ml in 0.62 M HCl) is added and mixed immediately. After a 10-min incubation at 37° C., the reaction is terminated with 25 μl of 2.8 N NaOH. The intensity of the fluorescent is measured using a fluorescent plate reader with excitation at 355 nm and emission read at 460 nm (Misko T P. et al. 1993). Results are expressed as means±S.D. (n=6). * indicates p<0.001 compared to the control group. As shown in FIG. 1**, coconut water extract and coconut shell extract have similar bioactivities, which significantly suppress the NO production by LPS-induced inflammation of RAW 264.7 cells.

Cell proliferation ability is assayed using a resazurin assay (Nociari M M. et al. 1998), in which resazurin dye is used as a redox indicator to detect cell growth, not cell death. 5 mM Resazurin sodium (Sigma, USA) stock solution in phosphate buffer saline (PBS) is prepared, and the working solution (50 μM) is diluted from the stock using DMEM high glucose (Gibco) without FBS. For resazurin assay, the culture medium is removed and freshly diluted resazurin working solution is added into each well. Following incubation at 37° C. in a humidified incubator of 5% $CO_2$-95% air for 2 hr, the resazurin dye is reduced by the activity of living cells, and the reduced form of resazurin is determined at a fluorescence excitation wavelength 530 nm and emission wavelength 590 nm by a Victor 2 1420 Multilable Counter (Wallac, PerkinElmer). The suppression effect of coconut water extract or coconut shell extract on LPS-induced inflammation (FIG. 1) does not result from cell number reducing, and there is no cytotoxicity of coconut water extract or coconut shell extract.

Example 3

Effect of Coconut Water Extract on TNF-α Gene Expression in TPA-Stimulated HaCaT Cells HaCaT cell line is a human keratinocyte cell line. The HaCaT cells ($2.5 \times 10^5$ cells/well; in 6-well plate) were first plated in DMEM high glucose (Gibco) containing 10% (v/v) fetal bovine serum (FBS; Gibco) on 96-well plate (Falcon) for 24 hours. Then the cultured medium was changed by DMEM high glucose (Gibco) containing 2% (v/v) fetal bovine serum (FBS; Gibco) on 96-well plate (Falcon) and cultured for 24 hours. Then treated with 2 ng/ml 12-O-tetradecanoyl-phorbol-13-acetate (TPA, Sigma) in the absence (control group) or presence of 0.1, 1, and 10 μg/ml coconut water extract. The normal group is treated with PBS.

Figure 2:
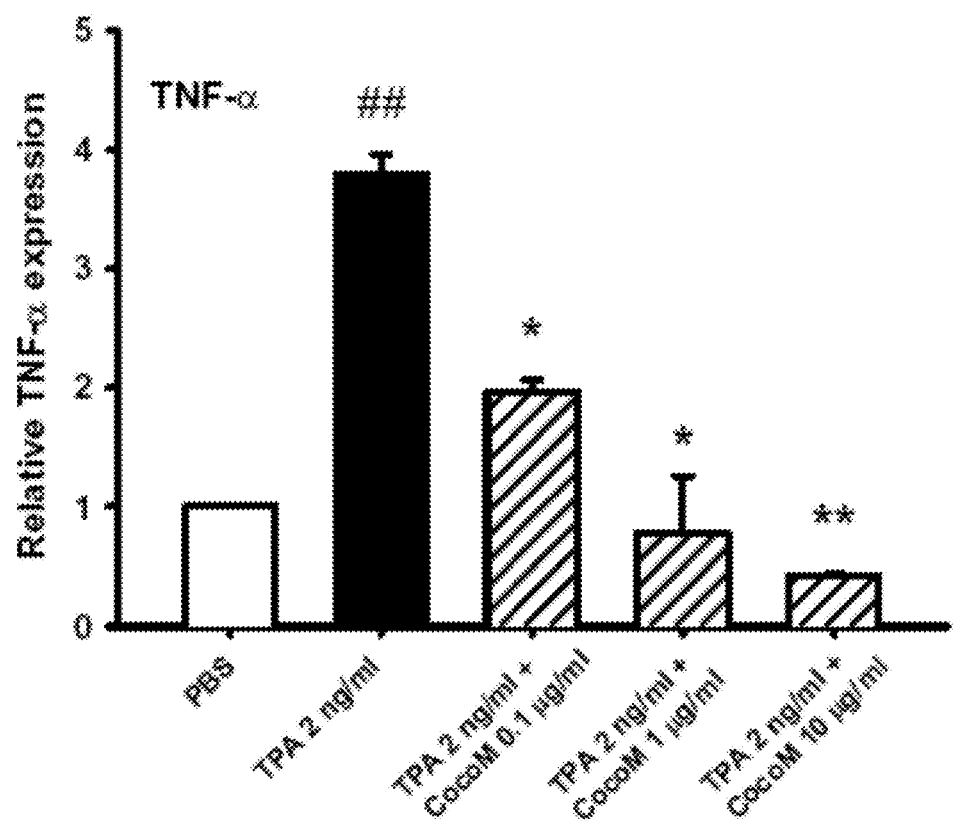
FIG. 2 is a diagram showing the effect of coconut water extract on TNF-α gene expression in TPA-stimulated HaCaT cells. The keratinocyte cell line HaCaT cells ($2.5 \times 10^5$ cells/well; in 6-well plate) were cultured in medium contain TPA (2 ng/ml) with different concentration of coconut water extract (0, 0.1, 1 and 10 μg/ml). After a 6 h incubation period with TPA and coconut water extract, the mRNA levels of TNF-α were analyzed by real-time-PCR. Results are expressed as means±S.D. (n=2). ## $P<0.01$ compared with PBS treatment. * $P<0.05$, ** $P<0.01$ compared to the absence of TPA.

After a 6 h incubation period, total ribonucleic acid (RNA) is isolated from HaCaT cells using RareRNA reagent (Bio-East, Taiwan) according to the manufacturer's instructions and converted into complementary deoxyribonucleic acid (cDNA) using Moloney murine leukemia virus reverse transcriptase (Promega). A total of 20 μl of the quantitative reverse transcription-polymerase chain reaction (RT-PCR) reaction mixture contained 1×SYBR GREEN PCR master mix are mixed with 0.5 μM each of primers and 3 μg cDNA. The primers targeting toward tumor necrosis factor-α (TNF-α) (SEQ ID NOs: 1 and 2) and GAPDH (SEQ ID NOs: 3 and 4) are shown in the Table 1. The reaction is carried out in a 96-well microtiter plate on an ABI PRISM 7500 Sequence Detector System (Applied Biosystems). The reaction mixture is first incubated at 50° C. for 2 min and 95° C. for 10 min, and followed by a 40-cycle amplification reaction. The steps of amplification reactions are denatured at 95° C. for 15 sec, followed by annealing at 55° C. for 40 s and extension at 72° C. for 40 s. The expression level of mouse GAPDH is used as an internal reference. Relative gene expression levels are calculated with the $2^{-\Delta\Delta C_T}$ method. Results are expressed as means±S.D. (n=2). ##P<0.01 compared with PBS treatment. *P<0.05, P<0.01 compared to the absence of TPA. As shown in FIG. 2**, 0.1, 1, and 10 μg/ml coconut water extract significantly suppressed TPA-induced TNF-α gene expression in TPA-stimulated HaCaT cells.

TABLE 1

| Primer Name | Sequence | SEQ ID NO: |
|---|---|---|
| TNF-α forward | 5'-CGG TGC CTA TGT CTC AGC CTC T-3' | 1 |
| TNF-α reverse | 5'-CAC TCC AGC TGC TCC TCC ACT T-3' | 2 |
| GAPDH forward | 5'-GCA AAT TCC ATG GCA CCG T-3' | 3 |
| GAPDH reverse | 5'-TCG CCC CAC TGA TTT TGG-3' | 4 |

Example 4

Effect of Coconut Water Extract on IL-10 and TGF-β Gene Expression in HaCaT Cells The HaCaT cells ($2.5 \times 10^5$ cells/well; in 6-well plate) were first plated in DMEM high glucose (Gibco) containing 10% (v/v) fetal bovine serum (FBS; Gibco) on 96-well plate (Falcon) for 24 hours. Then the cultured medium was changed by DMEM high glucose (Gibco) containing 2% (v/v) fetal bovine serum (FBS; Gibco) on 96-well plate (Falcon) and cultured for 24 hours. Then treated with 0.1, 1, and 10 μg/ml coconut water extract. The normal group is treated with PBS.

Figure 3A:
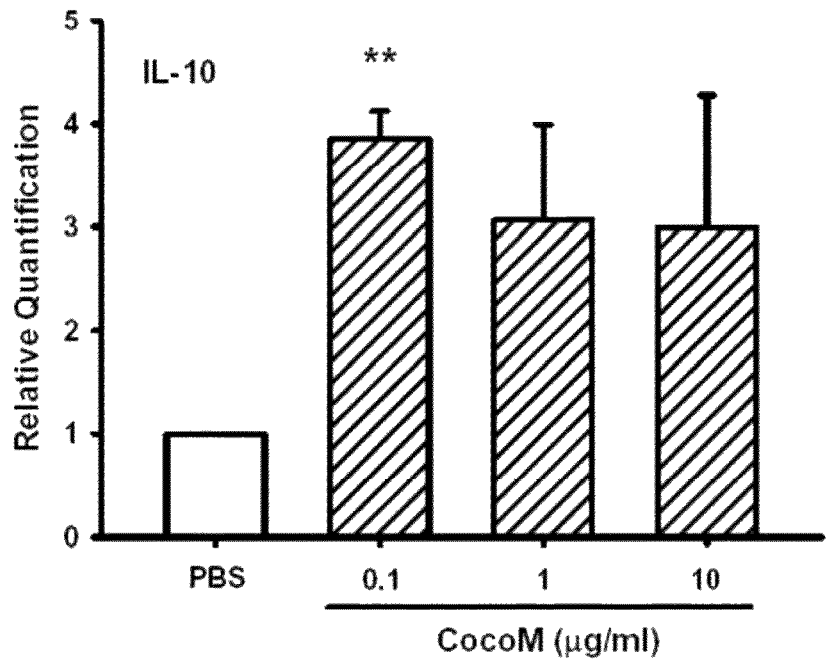
FIG. 3 is a diagram showing coconut water extract induce IL-10 and TGF-β mRNA expression in HaCaT cells. The keratinocyte cell line HaCaT cells ($2.5 \times 105$ cells/well; in 6-well plate) were cultured in medium contain coconut water extract (0, 0.1, 1 and 10 μg/ml). After a 6 h incubation period with coconut water extract, the mRNA levels of IL-10 and TGF-β were analyzed by real-time-PCR. Results are expressed as means±S.D. (n=2). ** $P<0.01$ compared with PBS only.
Figure 3B:
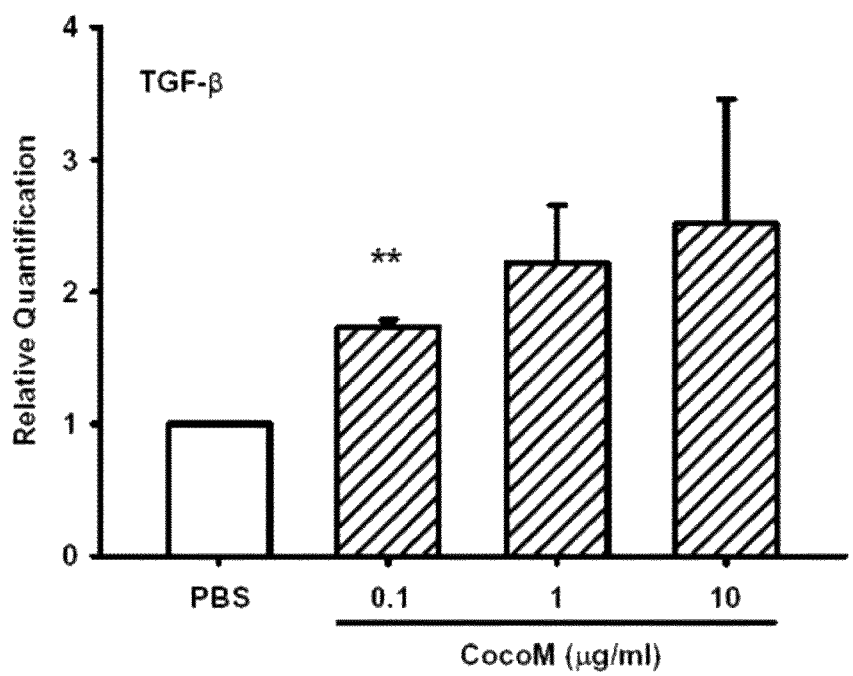

After a 6 h incubation period, total ribonucleic acid (RNA) is isolated from HaCaT cells using RareRNA reagent (Bio-East, Taiwan) according to the manufacturer's instructions and converted into complementary deoxyribonucleic acid (cDNA) using Moloney murine leukemia virus reverse transcriptase (Promega). A total of 20 μl of the quantitative reverse transcription-polymerase chain reaction (RT-PCR) reaction mixture contained 1×SYBR GREEN PCR master mix are mixed with 0.5 μM each of primers and 3 μg cDNA. The primers targeting toward interleukin 10 (IL-10) (SEQ ID NOs: 5 and 6), transforming growth factor beta (TGF-β) (SEQ ID NOs: 7 and 8) and GAPDH (SEQ ID NOs: 9 and 10) are shown in the Table 2. The reaction is carried out in a 96-well microtiter plate on an ABI PRISM 7500 Sequence Detector System (Applied Biosystems). The reaction mixture is first incubated at 50° C. for 2 min and 95° C. for 10 min, and followed by a 40-cycle amplification reaction. The steps of amplification reactions are denatured at 95° C. for 15 sec, followed by annealing at 55° C. for 40 s and extension at 72° C. for 40 s. The expression level of mouse GAPDH is used as an internal reference. Relative gene expression levels are calculated with the $2^{-\Delta\Delta CT}$ method. Results are expressed as means±S.D. (n=2). **P<0.01 compared with PBS only, As shown in FIG. 3, coconut water extract has the tendency to induce IL-10 (FIG. 3A) and TGF-β (FIG. 3B) gene expression in HaCaT cells.

TABLE 2

| Primer Name | Sequence | SEQ ID NO: |
|---|---|---|
| IL-10 forward | 5'-GCC TAA CAT GCT TCG AGA TC-3' | 5 |
| IL-10 reverse | 5'-TGA TGT CTG GGT CTT GGT TC-3' | 6 |
| TGF-β forward | 5'-AAA TGG ATA CAC GAA CCC AA-3' | 7 |
| TGF-β reverse | 5'-GCT GCA TTT GCA AGA CTT TAC-3' | 8 |
| GAPDH forward | 5'-GCA AAT TCC ATG GCA CCG T-3' | 9 |
| GAPDH reverse | 5'-TCG CCC CAC TGA TTT TGG-3' | 10 |

Example 5

Effect of Coconut Water Extract on TPA-Induced Ear Skin Inflammation Model

Female BALB/c mice of 8 weeks of age are purchased from the National Laboratory Animal Center (NLAC, Taiwan). For inducing skin inflammation in mice ear, mice are immunized via epicutaneous application of 80 μM 12-O-tetradecanoyl-phorbol-13-acetate (TPA, Sigma) to mouse ear in the absence (control group) or presence of two days orally pretreatment of 0.2, 1, and 5 mg/kg coconut water extract. The normal group is treated with PBS.

Figure 4:
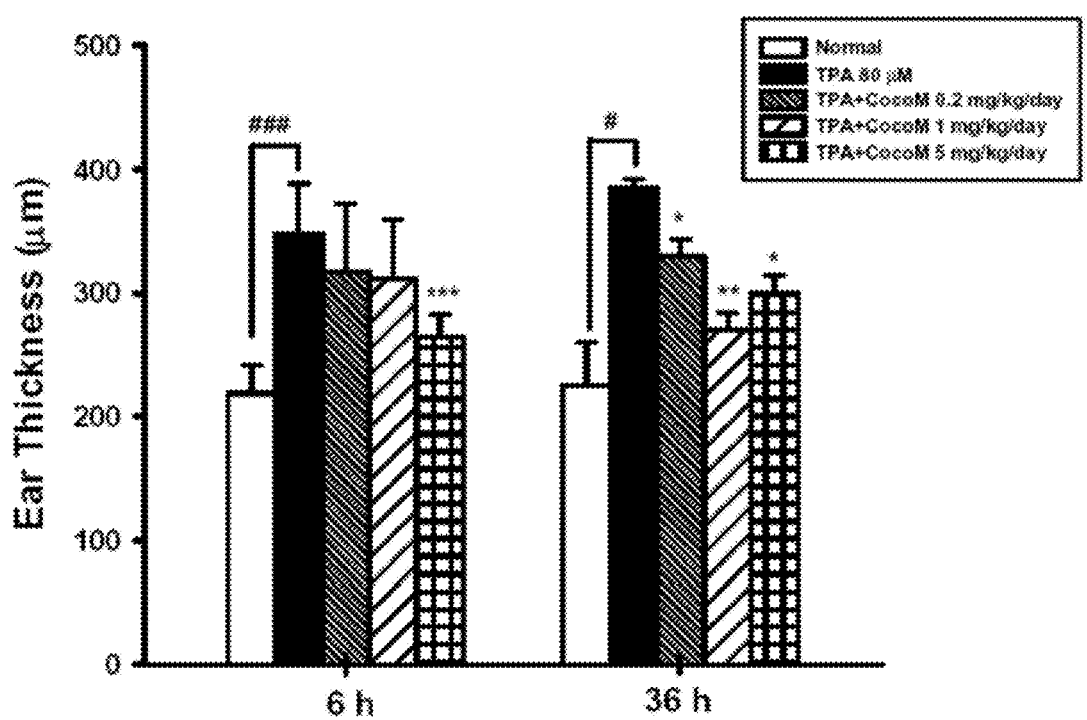
FIG. 4 is a diagram showing the effect of coconut water extract on TPA-induced ear thickness in mice. Epicutaneous application of TPA 80 μM to mouse ear resulted in induction of skin edema, and two days pretreatment with coconut water extract (0.2, 1 and 5 mg/kg/day) inhibited the induction of skin edema in a dose-dependent manner. Results are expressed as means±S.D. # $P<0.05$, ### $P<0.001$ compared with normal. * $P<0.05$,  $P<0.01$, * $P<0.001$ compared with TPA treatment only.

The mouse ear skin thickness was recorded after 6 hr and 36 hr TPA treatment (FIG. 4). Results are expressed as means±S.D. (n=2–6). #P<0.05, ###P<0.001 compared with normal. *P<0.05, P<0.01, *P<0.001 compared with TPA treatment only. As shown in FIG. 4, the TPA-induced mouse ear skin inflammation was significant suppressed by 5 mg/kg coconut water extract after 6 hr TPA treatment and 0.2, 1, 5 mg/kg coconut water extract after 36 hr TPA treatment.

Figure 5:
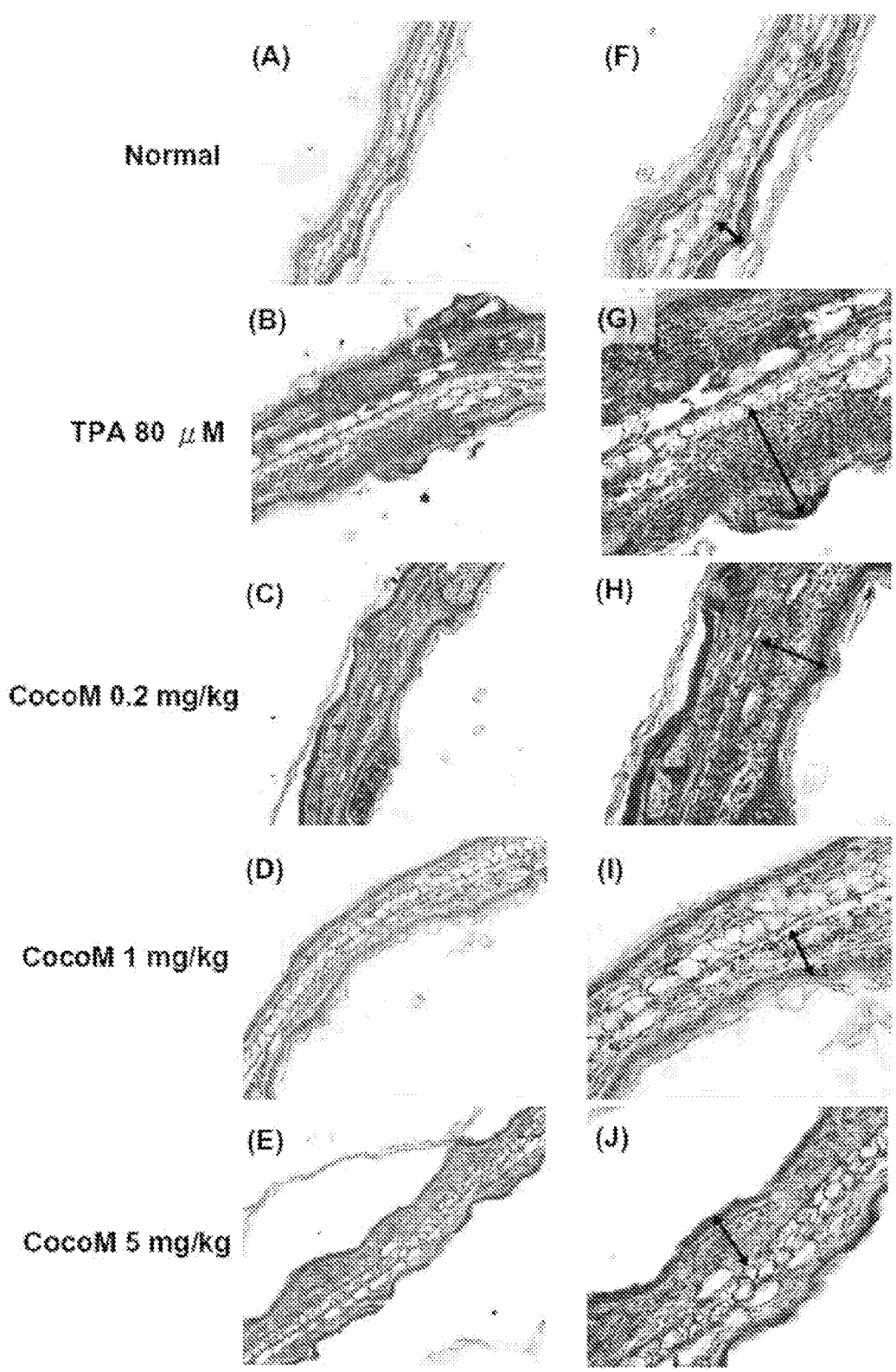
FIG. 5 is a diagram showing the effect of coconut water extract on TPA-induced ear edema and cell infiltration. The magnifications of FIG. 5A to 5E are 200×

The mouse ear skin biopsies was analysis by Hematoxylin and Eosin (H&E) staining after 36 hr TPA treatment (FIG. 5A to 5J). The magnification of FIG. 5A to 5E are 200; The magnification of FIG. 5F to 5J are 400. As showed in FIGS. 5B and 5G, 80 μM TPA treatment was significant induced skin edema in mouse ear compared with normal group (FIGS. 5A and 5F). And 0.2 (FIGS. 5C and 5H), 1 (FIGS. 5D and 5I), 5 (FIGS. 5E and 5J) mg/kg coconut water extract treatment significantly suppress the TPA-induced skin edema and reduce the inflammatory cell infiltration.

Example 6

Effect of Coconut Water Extract on Lipopolysaccharide-Induced Inflammation of Hepatocytes C57BL/6J Narl mice, 8-10 weeks of age, are purchased from National Laboratory Animal Center (NLAC, Taiwan) and used. The hepatocytes are isolated as previous description with modification (Kreamer B L. et al. 1986., Kojima T. et al. 2001., and Liu S. et al. 2002.). Mice are anaesthetized with Avertin (2% (w/v) 2,2,2-tribromoethanol, i.p. 300 mg/kg body weight) and the liver is perfused in situ through the inferior vena cava by using calcium-free Hank's balanced salt solution (HBSS) containing 0.5 mM Ethylene glycol-bis(2-aminoethylether)-N,N,N',N'-tetraacetic acid (EGTA; Sigma-Aldrich). The flow rate is 1 ml/min with the perfusate exiting via the severed portal vein. After 10 min of perfusion, HBSS containing 0.05% (w/v) collagenase (Type II; Worthington Biochemical Corporation) and 1 mM calcium chloride (Sigma-Aldrich) are added to the perfusion apparatus, and the perfusion is continued for 10 min at the same flow rate. The partially digested liver is removed, then put in a 60-mm culture dish (B D Falcon) containing HBSS and gently minced to open the liver capsule. The minced liver suspension is filtered through a nylon mesh (about 300 μm pore size) and then centrifugated at 50×g for 3 min to obtain the cell pellet. The cell pellet is suspended in DMEM medium (Gibco/Invitrogen) and centrifuged with the 35% (v/v) percoll (GE Healthcare) medium at 50×g for 5 min. The cell pellet is further washed twice or thrice with DMEM medium by centrifugation at 50×g for 3 min for obtaining hepatocytes.

The isolated hepatocytes are plated at approximately $1\times10^4$ cells/well with DMEM medium (Gibco/Invitrogen) containing 10% FBS (Gibco) on 96-well plates (Costar) and then cultured at 37° C. in a humidified incubator of 5% $CO_2$-95% air. The hepatocytes are then treated with 1 or 10 μg/ml lipopolysaccharide (LPS; Sigma, USA) in the absence (control group) or presence of 0.1 and 1 μg/ml coconut water extract in DMEM (Gibco) containing 2% (v/v) FBS (Gibco) the next day. The normal group is hepatocytes treated with neither LPS nor coconut water extract. After a 24-h incubation period, supernatants are analyzed for nitric oxide (NO) production by DAN assay while cell viability is examined by resazurin assay.

Figure 6:
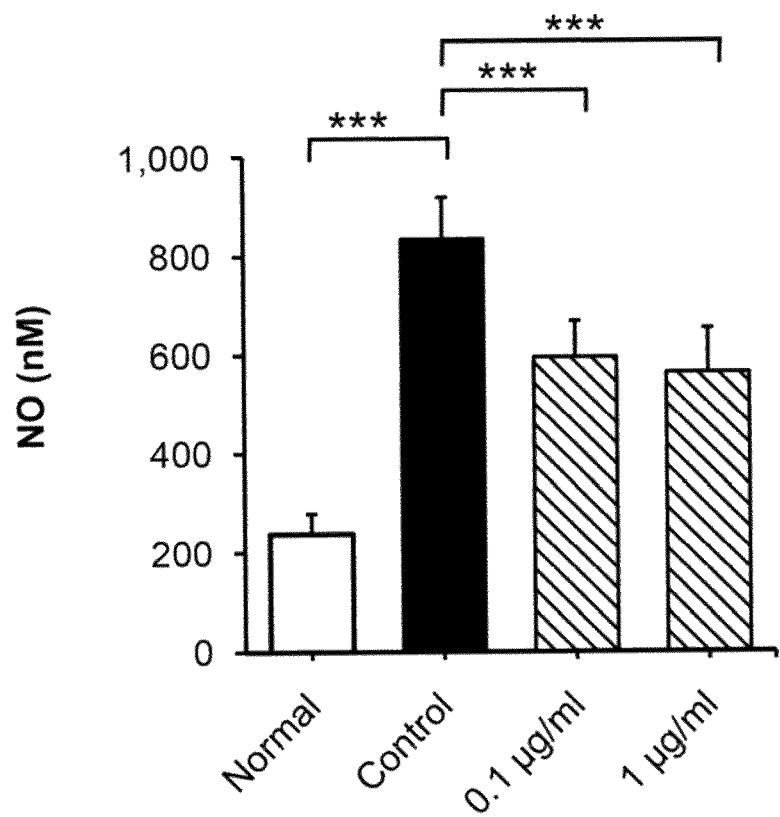
FIG. 6 is a diagram showing the effect of coconut water extract on lipopolysaccharide-induced inflammation of hepatocytes. The control group is hepatocytes administered with lipopolysaccharide (LPS) to induce inflammation. The treatment groups are administered with LPS in the presence of 0.1 and 1 μg/ml coconut water extract. The normal group is treated with neither LPS nor coconut water extract. Nitric oxide (NO) production, the inflammation marker, is measured by DAN assay. Results are expressed as means±S.D. (n=6). *** indicates $p<0.001$.

NO participates in liver inflammation and thus can be used as a marker to evaluate the effect on the inflammation. 2,3-Diaminonaphthalene (DAN; Sigma, USA) is reduced with nitrte under acidic conditions to form 1-(H)-naphthotriazole, a fluorescent product. 100 μl of sample is first brought to plate. 50 μl of freshly prepared DAN (0.05 mg/ml in 0.62 M HCl) is added and mixed immediately. After a 10-min incubation at 37° C., the reaction is terminated with 25 μl of 2.8 N NaOH. The intensity of the fluorescent is measured using a fluorescent plate reader with excitation at 355 nm and emission read at 460 nm (Misko T P. et al. 1993). Results are expressed as means±S.D. (n=6). *** indicates p<0.001 compared to the control group. As shown in FIG. 6, both 0.1 and 1 μg/ml coconut water extract significantly suppress the NO production of LPS-induced hepatic inflammation.

Cell proliferation ability is assayed using a resazurin assay (Nociari M M. et al. 1998), in which resazurin dye is used as a redox indicator to detect cell growth, not cell death. Resazurin sodium (Sigma, USA) stock solution in PBS (5 mM) is prepared, and the working solution (50 μM) is diluted from the stock using DMEM without FBS. For resazurin assay, the culture medium is removed and freshly diluted resazurin working solution is added into each well. Following incubation at 37° C. in a humidified incubator of 5% $CO_2$-95% air for 2 hr, the resazurin dye is reduced by the activity of living cells, and the reduced form of resazurin is determined at a fluorescence excitation wavelength 530 nm and emission wavelength 590 nm by a Victor 2 1420 Multilable Counter (Wallac, PerkinElmer). There is no cytotoxicity on coconut water extract administrated hepatocytes. Accordingly, coconut water extract is effective in treating inflammation.

Example 7

Effect of Coconut Water Extract on Liver Injury in D-GalN/LPS-Induced Liver Inflammation Male C57BL/6J Narl mice of 8 weeks of age are purchased from the National Laboratory Animal Center (NLAC, Taiwan). For preparation of LPS/D-GalN induced acute liver inflammation (Yamada I. et al. 2008.), mice are given an i.p. injection of phosphate-buffered saline (PBS) containing D-Galactosamine (D-GalN; Sigma, USA) (600 mg/kg body weight) and lipopolysaccharide (LPS; Sigma, USA) (8 µg/kg body weight). Coconut water extract (0.2 and 1 mg/kg body weight) in boiled water is administered twice orally, at 24 h and 30 min before the LPS/D-GalN co-injection, while equal volume of boiled water is given to the control group. For normal group, mice are i.p. injected with PBS in volumes equal to those used for the D-GalN and LPS injections. Serum samples and liver tissues are collected 3 hr after the LPS/D-GalN co-injection for analyzing serum transaminase activity and mRNA levels, respectively.

Figure 7A:
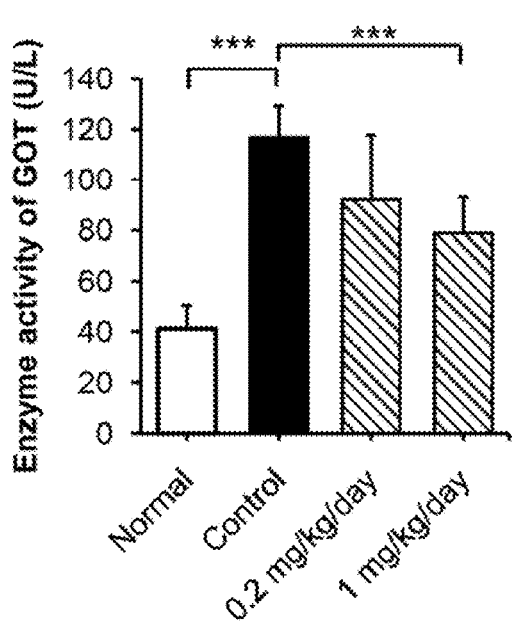
FIG. 7A is a diagram showing the effect of coconut water extract on liver injury in D-GalN/LPS-induced liver inflammation mice model. The control group is administered with D-Galactosamine (D-GalN) and lipopolysaccharide (LPS) to induce liver inflammation. The normal group is given phosphate buffer saline (PBS) instead of D-GalN and LPS. The treatment groups are administered with GalN and LPS and fed with coconut water extract at the dose of 0.2 and 1 mg/kg/day. Serum glutamic oxaloacetic transaminase (GOT) activity is determined. Results are expressed as means±S.D. (n=4–6). *** indicates $p<0.001$.
Figure 7B:
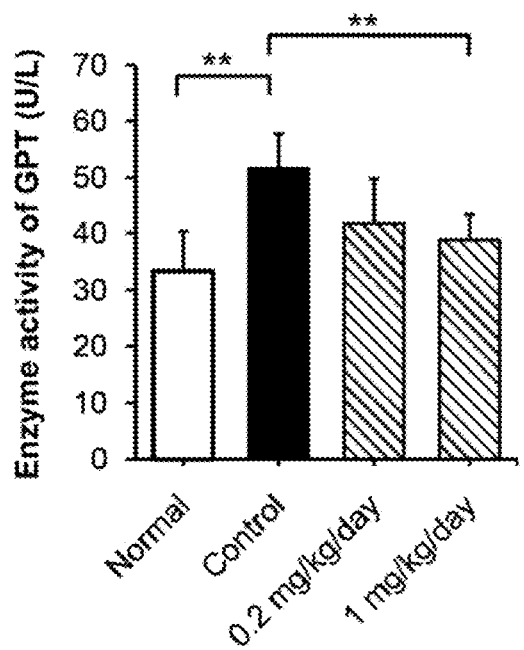
FIG. 7B is a diagram showing the effect of coconut water extract on liver injury in D-GalN/LPS-induced liver inflammation mice model. Serum glutamic pyruvic transaminase (GPT) activity is determined. Results are expressed as means±S.D. (n=4–6). ** indicates $p<0.01$.

Liver damage is assessed by measuring serum enzyme activities of alanine aminotransferase (ALT) (also named glutamic pyruvic transaminase, GPT) and aspartate aminotransferase (AST) (also named glutamic oxaloacetic transaminase, GOT) using GPT (ALAT) IFCC mod. and GOT (ASAT) IFCC mod. (HUMAN GmbH, Germany) kits, respectively, according to the manufacturer's instructions. Results are expressed as means±S.D. (n=4–6).  indicates p<0.01 and * indicates p<0.001, compared to the control group. As shown in FIGS. 7A and 7B, 0.2 mg/kg coconut water extract significantly suppresses GPT levels while 1 mg/kg coconut water extract significantly suppresses both GOT and GPT levels in D-GalN/LPS-induced liver inflammation.

Figure 7C:
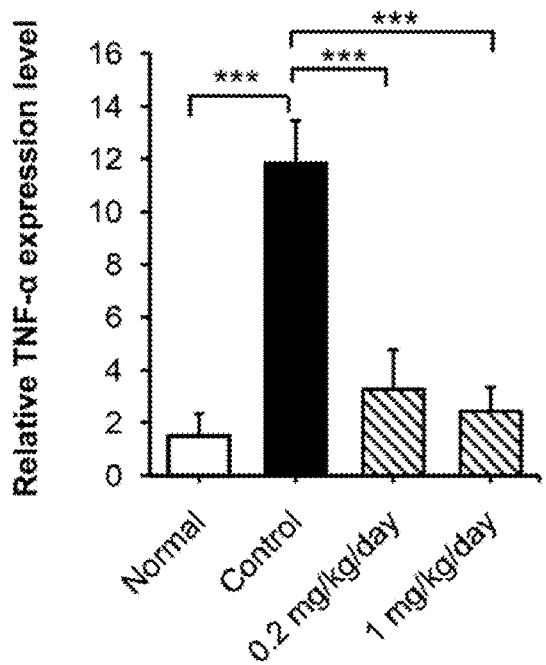
FIG. 7C is a diagram showing the effect of coconut water extract on TNF-α expression in D-GalN/LPS-induced liver inflammation mice model. The mRNA levels of TNF-α are determined by real-time PCR. Results are expressed as means±S.D. (n=4–6). *** indicates p<0.001.

Total ribonucleic acid (RNA) is isolated from liver tissue using RareRNA reagent (Bio-East, Taiwan) according to the manufacturer's instructions and converted into complementary deoxyribonucleic acid (cDNA) using Moloney murine leukemia virus reverse transcriptase (Promega). A total of 20 µl of the quantitative reverse transcription-polymerase chain reaction (RT-PCR) reaction mixture contained 1×SYBR GREEN PCR master mix are mixed with 0.5 µM each of primers and 3 µg cDNA. The primers targeting toward tumor necrosis factor-α (TNF-α) (SEQ ID NOs: 11 and 12) and β-actin (SEQ ID NOs: 13 and 14) are shown in the Table 3. The reaction is carried out in a 96-well microtiter plate on an ABI PRISM 7500 Sequence Detector System (Applied Biosystems). The reaction mixture is first incubated at 50° C. for 2 min and 95° C. for 10 min, and followed by a 40-cycle amplification reaction. The steps of amplification reactions are denatured at 95° C. for 15 sec, followed by annealing at 55° C. for 40 s and extension at 72° C. for 30 s. The expression level of mouse β-actin is used as an internal reference. Relative gene expression levels are calculated with the $2^{-\Delta\Delta C_T}$ method. Results are expressed as means±S.D. (n=4–6). *** indicates p<0.001 compared to the control group. As shown in FIG. 7C, both 0.2 and 1 mg/kg coconut water extract significantly suppress TNF-α expression of D-GalN/LPS-induced liver inflammation. According to the results of FIG. 7A to 7C, coconut water extract administration has therapeutically effects on liver inflammation (injury). Furthermore, the TNF-α suppression effect of coconut water extract can be used for treating TNF-α associated immunological diseases and/or disorders.

TABLE 3

| Primer Name | Sequence | SEQ ID NO: |
|---|---|---|
| TNF-α forward | 5'-CCA GGC AGT CAG ATC ATC TTC TC-3' | 11 |
| TNF-α reverse | 5'-AGC TGG TTA TCT CTC AGC TCC AC-3' | 12 |
| β-actin forward | 5'-GTG GGC CGC CCT AGG CAC CA-3' | 13 |
| β-actin reverse | 5'-TGG CCT TAG GGT TCA GGG GG-3' | 14 |

Example 8

Figure 8:
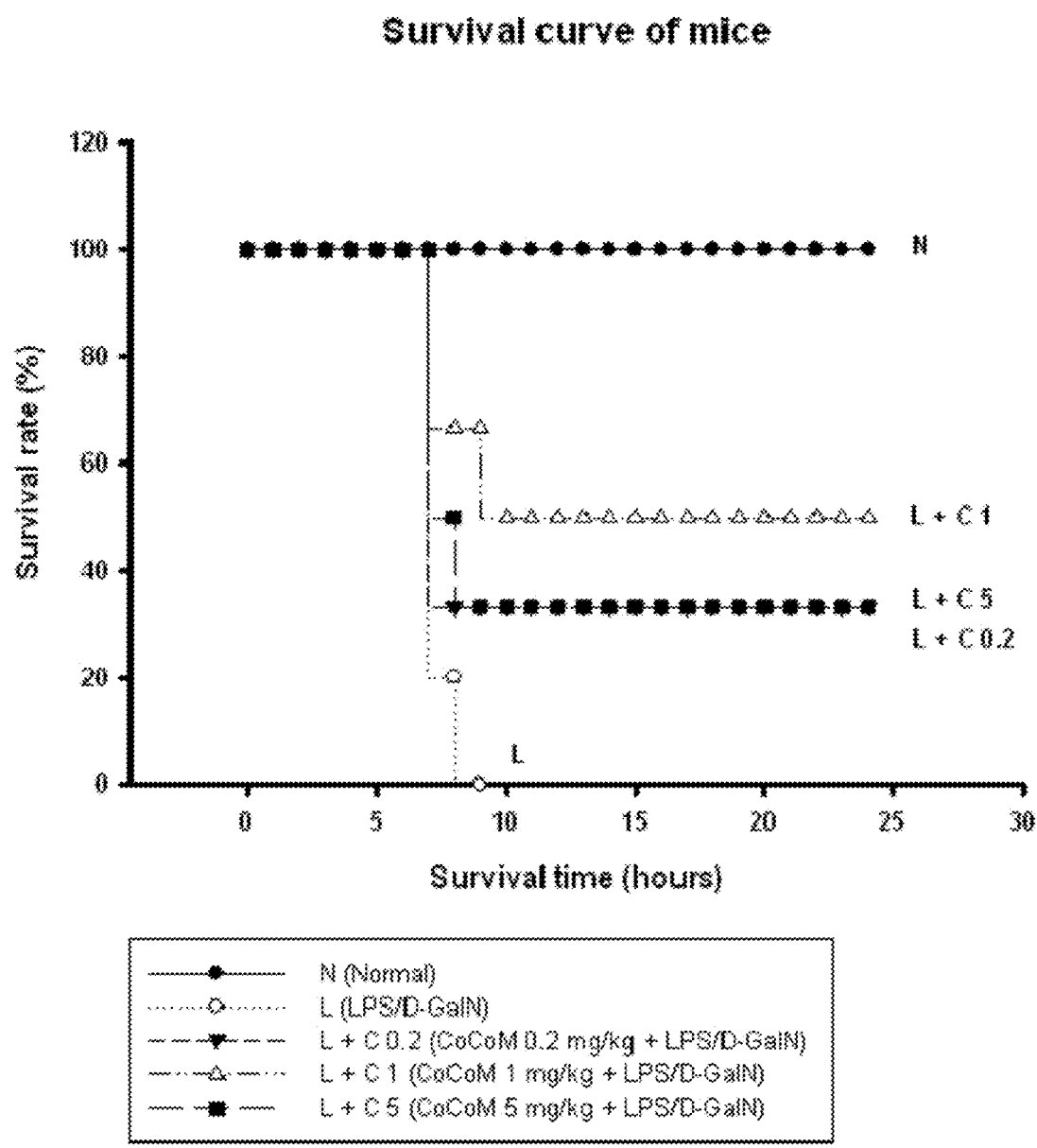
FIG. 8 is a disgram showing the effects of coconut water extract on the survival curve of mice after LPS/D-GalN co-injection. Each group consisted of 6 to 8 mice. Mice were intraperitoneally injected with D-GalN (600 mg/kg body weight) and LPS (8 µg/kg body weight). Coconut water extract (0.2, 1, 5 mg/kg body weight) was orally administrated at 24 h and 30 min before D-GalN and LPS injection.

Effect of Coconut Water Extract on Survival Rate of Mice after D-GalN/LPS-Induced Liver Inflammation Male C57BL/6J Narl mice of 9 weeks of age are purchased from the National Laboratory Animal Center (NLAC, Taiwan). For preparation of LPS/D-GalN induced acute liver inflammation (Yamada I. et al. 2008.), mice are given an i.p. injection of phosphate-buffered saline (PBS) containing D-Galactosamine (D-GalN; Sigma, USA) (600 mg/kg body weight) and lipopolysaccharide (LPS; Sigma, USA) (8 µg/kg body weight). Coconut water extract (0.2, 1 and 5 mg/kg body weight) in boiled water is administered twice orally, at 24 h and 30 min before the LPS/D-GalN co-injection, while equal volume of boiled water is given to the control group. For normal group, mice are i.p. injected with PBS in volumes equal to those used for the D-GalN and LPS injections. As shown in FIG. 8, 0.2, 1 and 5 mg/kg coconut water extract significantly suppress death rate in D-GalN/LPS-induced liver inflammation mice.

Example 9

Preparation of Proteoglycan

Proteoglycan of porcine articular cartilage is prepared as previously described with modification (Finnegan A. et al. 1999. and Glant T T. and Mikecz K. 2004.). Briefly, cartilage pieces are frozen at −70° C., ground by a pulverizer, and then extracted with 4 M guanidium hydrochloride (Sigma, USA), 10 mM EDTA (Sigma, USA), 2 mM phenylmethylsulfonyl fluoride (PMSF; Sigma, USA), 2 mM iodoacetamide (Sigma, USA), and 5 µg/mL pepstatin A (Sigma, USA) at 4° C. After 24 hours, the extraction is collected and centrifuged at 2000×g for 40 min to obtain the supernatant. The supernatant is further centrifuged in cesium chloride (1.5 g/ml; Sigma, USA) gradient at 75000×g at 4° C. for 48 hours to collect the fraction with density higher than 1.56 g/ml. After dialyzed (using snake skin pleated dialysis tubing 3500 MW; Pierce) against 0.1 M sodium acetate (Sigma, USA) at pH 7.4 and deionized H$_2$O for four times each at 4□, the fraction is lyophilized to obtain the crude proteoglycan extract and the production rate is 0.51%.

The crude proteoglycan extract is dissolved in buffer solution containing 50 mM Tris (UBS, USA) and 60 mM sodium acetate (Sigma, USA) at pH 8.0 and then digested with condroitinase ABC (1 unit; Sigma, USA) at 37° C. for 24 hours. After digestion, the buffer is adjusted to pH 5.8, and the proteoglycan is further digested with keratinase (5.6 units; Sigma, USA) at 37° C. for 24 hours. After digestion with condroitinase and keratinase, the crude proteoglycan extract is dialyzed against deionized $H_2O$ and lyophilized to obtain the deglycosylated proteoglycan (proteoglycan depleted of glycosaminoglycan side chains), named proteoglycan followed in this specification. The proteoglycan is analyzed and checked by 12% denatured sodium dodecyl sulfate polyacrylamide gel electrophoresis (SDS-PAGE; data not shown). The production rate of proteoglycan is about 19.13%.

Example 10

Effect of Coconut Water Extract on Proteoglycan-Induced Arthritis Model

Proteoglycan-induced arthritis model (an rheumatoid arthritis model) is performed as previously described with modification (Finnegan A. et al. 1999. and Glant T T. and Mikecz K. 2004.). Female BALB/c mice of 8-10 weeks of age are purchased from the National Laboratory Animal Center (NLAC, Taiwan). For proteoglycan-induced arthritis group, mice are immunized via intraperitoneal (i.p.) injection with the proteoglycan emulsion (phosphate buffer saline (PBS) containing 100 or 50 μg proteoglycan and 1 mg dimethyldioctadecylammonium bromide (DDA; Sigma, USA) adjuvant) on the day 0, 14, 28, 42 and 63. Coconut water extract is administered 0.2, 1 and 5 mg/kg/day in diet (0.2, 1 and 5 mg/kg/day group, respectively) from day 14 to the end of the experiment. For normal group, PBS injections of corresponding volumes are given i.p. in parallel and administered standard diet (LabDiet®) to the mice. At day 77, mice are sacrificed.

Figure 9A:
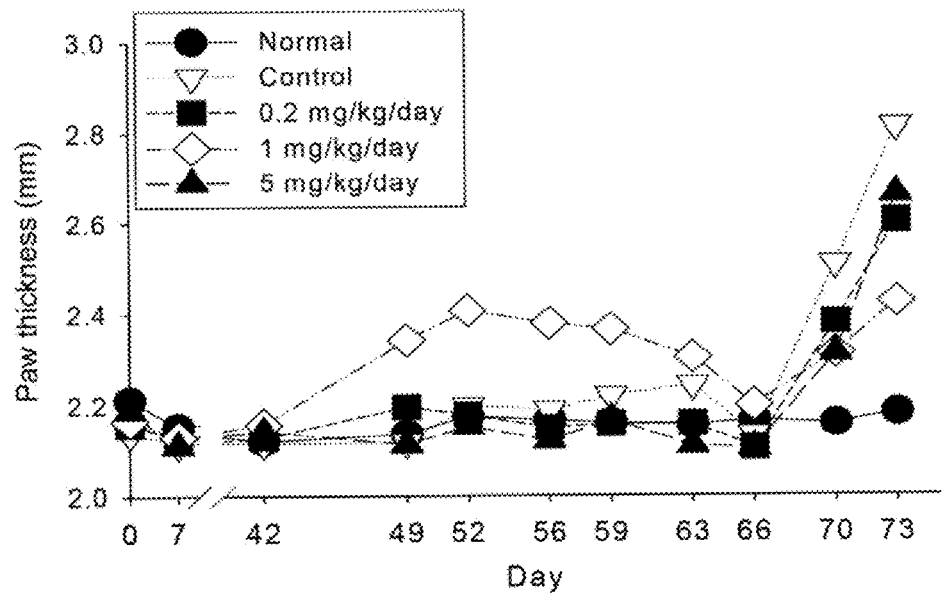
FIG. 9A is a diagram showing the effects of coconut water extract on the paw thickness in proteoglycan-induced arthritis mice model. The control group is administered with the proteoglycan to induce arthritis. The normal group is given phosphate buffer saline (PBS) instead of the proteoglycan. The treatment groups are administered with proteoglycan and fed with coconut water extract at the dose of 0.2, 1 and 5 mg/kg/day.
Figure 9B:
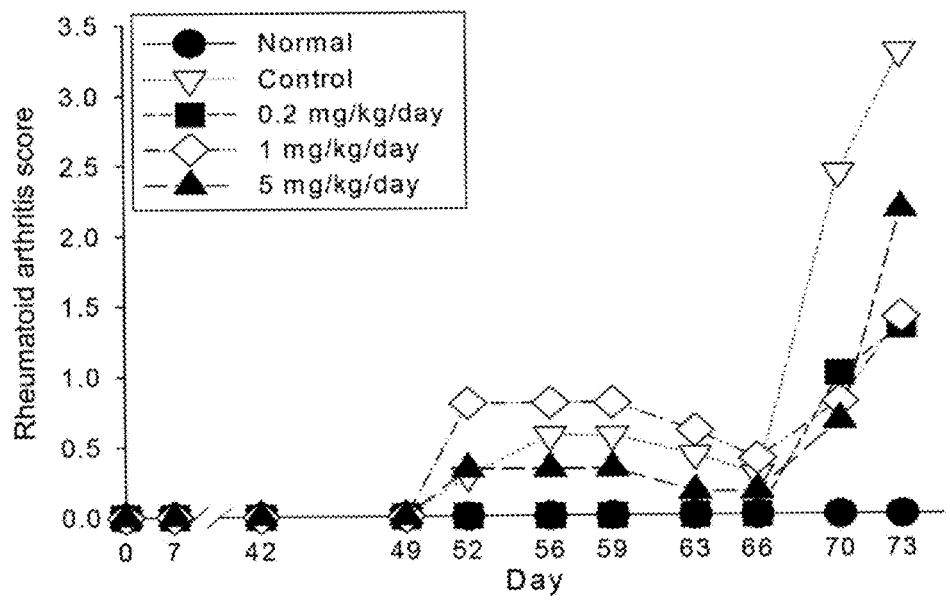
FIG. 9B is a diagram showing the effects of coconut water extract on the rheumatoid arthritis score in proteoglycan-induced arthritis mice model. The coconut water extract is administered at the dose of 0.2, 1 and 5 mg/kg/day.

The incidence and paw thickness of 5 mg/kg/day group are rising rapidly as the control group at the end of the experiment, and the final incidence is also about 85% (FIGS. 9A and 9B). The final incidence of 1 mg/kg/day group is around 40% (FIGS. 9A and 9B). The paw thickness of 1 mg/kg/day group raises just slightly after the last injection of proteoglycan, and begins to lower after day 73 (FIG. 9A). Both the paw swollen and clinical symptoms of arthritis of 1 mg/kg/day group are the slightest among the three coconut water extract treated groups (FIGS. 9A and 9B). The incidence of 0.2 mg/kg/day group raises to about 50% after the last injection of proteoglycan and decreases at the end of the experiment. The paw swollen of 0.2 mg/kg/day group also increases after the last injection of proteoglycan and begins to lower after day 73 as well as 1 mg/kg/day group (FIG. 9A). In addition, during the experiment, the paw thickness and clinical symptoms of rheumatoid arthritis are significantly lower than control group (FIGS. 9A and 9B).

Coconut water is used for nutritional formulation beverages and food products, lowering the fever, and as a remedy for gastroenteritis, urinary stone dissolution and coronary heart disease in folk medicine (Mandal S M. et al. 2009.). In addition, coconut water is reported to have inhibitory activity against human bacterial pathogens and antiulcerogenic effects (Mandal S M. et al. 2009. and Nneli R O. and Woyike O A. 2008.). Accordingly, coconut water might have some unclear effects on immune response.

Coconut water extract is proved in this application to suppress TNF-α and NO production, which are associated with inflammation or autoimmune diseases and to induce IL-10 and TGF-β production, which are associated with resolution of inflammation. (Lawrence T. and Gilroy D. W. 2007., Serhan C. N. et al. 2007.) In addition, coconut water extract has therapeutic effect on skin inflammation, liver inflammation and, rheumatoid arthritis especially at low dose (e.g. lower than 2 mg/kg/day), and therefore it does have immunosuppressive effect on immunological diseases and/or disorders, for instance, the inflammatory and autoimmune diseases. This application proves that coconut water extract or coconut shell extract can be used to treat immunological diseases and/or disorders and to suppress the clinical symptoms of inflammation thereof.

The therapeutic dose of 2 mg/kg/day coconut water extract for arthritis mice is equal to 0.162 mg/kg/day for human of 60 kg weight (Reagan-Shaw S. et al. 2008.). Because there is about 20 mg coconut water extract in one coconut fruit (with about 500 ml coconut water), the therapeutic dose of 2 mg/kg/day coconut extract for human is equal to about 243 ml coconut water per day, about a half coconut fruit, which approximates to the use in the folk medicine. Accordingly, even high dose (e.g. 50 mg/kg/day coconut water extract) administration will not cause the side-effects, such as inhibition in immune cell proliferation and hematopoiesis, present in ordinary immunosuppressive treatment.

There are still many immunological diseases and/or disorders need to be treated by anti-inflammatory or immunosuppressive treatment, for instance, skin inflammation, liver inflammation, arthritis diseases (such as rheumatoid arthritis, osteoarthritis, polyarteritis nodosa, and acute gouty arthritis), allergy (such as asthma, eczema (atopic dermatitis), allergic rhinitis, and ocular allergy), cryoglobulinemia, idiopathic thrombocytopenic purpura, systemic vasculitis, autoimmune hemolytic anemia, Raynaud's phenomenon, systemic lupus erythematosus, scleroderma (systemic sclerosis), insulin-dependent diabetes mellitus (IDDM), inflammatory bowel diseases (such as Crohn's disease) (Koo A P. 2000, Davidson A. and Diamond B. 2001, and Kim E Y. and Moudgil K D. 2008), sepsis, septic shock (Annane D. et al. 2009), psoriasis (Menter A. et al. 2009), and Behcet's disease (Sakane T. et al. 1999). Therefore, coconut water extract or coconut shell extract administering can be beneficial for all these immunological diseases and/or disorders without the drawbacks of anti-inflammatory or immunosuppressive therapy.

In addition, coconut water extract or coconut shell extract is proved in this application to suppress TNF-α. TNF-α is a cytokine produced by numerous cell types, including monocytes and macrophages, that was originally identified based on its capacity to induce the necrosis of certain mouse tumors. Subsequent analyses of the effects of TNF-α have confirmed that TNF plays a central role in the proinflammatory cytokine network. Many of the hallmarks of chronic inflammation, such as leukocyte recruitment, activation and proliferation, and the production of inflammatory mediators, have had their mechanistic link to TNF empirically confirmed (Tracey D. et al. 2008). TNF-α is implicated in the pathogenesis of many inflammatory diseases and disorders while anti-TNF-α therapy is used for these, such as rheumatoid arthritis, psoriasis and psoriatic arthritis, juvenile chronic arthritis, ankylosing spondylitis, inflammatory bowel disease (including Crohn's disease), ulcerative colitis, Behcet's disease, juvenile idiopathic arthritisvasculitis, uveitis (Valesini G. et al. 2007, Wong M. et al. 2008 and Lin J. et al. 2008), adult Still's disease, Wegener's granulomatosis, scleroderma, Sjögren's syndrome, sarcoidosis, pyoderma gangrenosum, and polymyositis/dermato myositis (Tutuncu Z. et al. 2002). Therefore, coconut water extract or coconut shell extract can be used for treating these TNF-α associated diseases and/or disorders.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

LIST OF REFERENCES

Alviano D S. et al. 2004. *J Ethnopharinacol.* 92:269-273.
Andrade E R. et al. 2002. *Small Rum.* 43:235-243.
Annane D. et al. 2009. *JAMA.* 301:2362-2375.
Apostolaki M, Armaka M, Victoratos P et al. 2010. *Curr Dir Autoimmun* 11: 1-26
Bonifati C. et al. 1994. *Clin Exp Dermatol* 19, 383-387.
Campbell-Falck D. et al. 2000. *Am. J. Emerg. Med.* 18:108-111.
Davidson A and Diamond B. 2001. *N Engl J Med.* 345:340-350.
Erhardt A. et al. 2010. *Digestive Diseases.* 28(1):86-92.
Esquenazi D. et al. 2002. *Res Microbiol.* 153:647-652.
Ettehadi P et al. 1994. *Clin Exp Immunol* 96, 146-151.
Figueiredo J. R. 2000. *Theriogenology* 54:809-822.
Finnegan A. et al. 1999. *J Immunol* 163:5383-5390.
Gaffo A. et al. 2006. *Am J Health Syst Pharm.* 63:2451-2465.
Gary S. and Firestein, M. 2003. *Nature* 423:356-361.
Gary S. and Firestein, M. 2005. *J. Clin. Rheumatol.* 11:S39-S44.
Giant T T. and Mikecz K. 2004. *Methods Mol. Med.* 102:313-338.
Groves, R. et al. 2004. *Cytokine* 28, 162-166.
Kim E Y. and Moudgil K D. 2008. *Immunol Lett.* 120:1-5.
Kojima T. et al. 2001. *Am J Physiol Gastrointest Liver Physiol.* 281:G1004-1013.
Koo A P. 2000. *J Clin Apher.* 215:18-27.
Kreamer B L. et al. 1986. *In Vitro Cell Dev Biol.* 22:201-211.
Lawrence T. and Gilroy D. W. 2007. *Int J Exp Pathol.* 88:85-94
Lin J. et al. 2008. *Clin Immunol.* 126:13-30.
Liu S. et al. 2002. *Infect Immun.* 70:3433-3442.
Mandal S M. et al. 2009. *Peptides.* 30:633-637.
Mantena S K. et al. 2003. *Nahrung.* 47:126-131.
Mendonça-Filho R R. et al. 2004. *Res Microhiol.* 155:136-143.
Menter A. et al. 2009. *J Am Acad Dermatol.* 61:451-485.
Misko T P. et al. *Anal Biochem.* 1993. 214:11-16.
Nneli R O. and Woyike O A. 2008. *Phytother Res.* 22:970-972.
Nociari M M. et al. 1998. *J. Immunol. Methods.* 213:157-167.
Ramadori G. et. al. 2008. *Journal of Physiology & Pharmacology.* 59-1:107-17.
Reagan-Shaw S. et al. 2008. *FASEB J.* 22:659-661.
S. Kintzios. et al. 2000. *Scientia Hort.* 85:137-144.
Santoso U. et al. 1996. *Food Chem.* 57:299-304.
Sakane T. et al. 1999. *N Engl J Med.* 341:1284-1291.
Serhan C. N. et al. 2007. *FASEB J* 21:325-332
Tiainen, T. 1993. *Plant Sci.* 88:83-90.
Tracey D. et al. 2008. *Pharmacol Ther.* 117:244-279.
Tutuncu Z. et al. 2002. *Clin Exp Rheumatol.* 20(6 Suppl 28):S146-51.
Valesini G. et al. 2007. *Autoimmun Rev.* 7:35-41.
Wong M. et al. 2008. *Clin Immunol.* 126:121-136.
Yamada I. et al. 2008. *Cytokine.* 41:293-301.

What is claimed is:

1. A method for treating immunological disorders associated with tumor necrosis factor-alpha (TNF-α) in a subject in need thereof, comprising administering to the subject a therapeutically effective amount of 0.2 mg/kg/day to 5 mg/kg/day of a coconut (*Cocos nucifera* Linn.) water extract or a coconut (*Cocos nucifera* Linn.) shell extract, wherein the extract induces transforming growth factor beta (TGF-β) or interleukin-10 (IL-10) as an endogenous immunosuppressive factor, and wherein the immunological disorders are at least one selected from the group consisting of skin inflammation, liver inflammation, and rheumatoid arthritis.

2. The method of claim 1, wherein the coconut (*Cocos nucifera* Linn.) water extract or the coconut (*Cocos nucifera* Linn.) shell extract is prepared by a process comprising:
   (a) passing coconut water or coconut shell water through a resin absorption chromatographic column, wherein the coconut shell water is obtained by adding water to coconut shell;
   (b) washing out the column with water; and
   (c) eluting the column by any combination of solutions or solvents capable of desorbing the coconut water extract or the coconut shell extract from the column.

3. The method of claim 2, wherein the desorbing solutions or solvents are organic solvents, water, or any combination thereof.

4. The method of claim 3, wherein the organic solvent is at least one selected from the group consisting of methanol, ethanol, acetonitrile, acetone, isopropanol, and any combination thereof.

5. The method of claim 4, wherein the organic solvent is at least one selected from the group consisting of methanol, ethanol, and any combination thereof.

6. The method of claim 1, wherein the subject has skin inflammation.

7. The method of claim 1, wherein the subject has liver inflammation.

8. The method of claim 1, wherein the subject has rheumatoid arthritis.

9. The method of claim 1, wherein the therapeutically effective amount of the coconut (*Cocos nucifera* Linn.) water extract or the coconut (*Cocos nucifera* Linn.) shell extract administered has a transforming growth factor beta (TGF-β) or interleukin-10 (IL-10) inducing effect as an endogenous immunosuppressive factor for treating immunological disorders.

* * * * *

SEQUENCE LISTING

```
<160> NUMBER OF SEQ ID NOS: 14

<210> SEQ ID NO 1
<211> LENGTH: 22
<212> TYPE: DNA
<213> ORGANISM: Artificial Sequence
<220> FEATURE:
<223> OTHER INFORMATION: Synthesized DNA fragment of forward primer for
      tumor necrosis factor-alpha

<400> SEQUENCE: 1
cggtgcctat gtctcagcct ct                                            22

<210> SEQ ID NO 2
<211> LENGTH: 22
<212> TYPE: DNA
<213> ORGANISM: Artificial Sequence
<220> FEATURE:
<223> OTHER INFORMATION: Synthesized DNA fragment of reverse primer for
      tumor necrosis factor-alpha

<400> SEQUENCE: 2
```
cactccagct gctcctccac tt                                                22

<210> SEQ ID NO 3
<211> LENGTH: 19
<212> TYPE: DNA
<213> ORGANISM: Artificial Sequence
<220> FEATURE:
<223> OTHER INFORMATION: Synthesized DNA fragment of forward primer for
      glyceraldehyde-3-phosphate dehydrogenase (GAPDH)

<400> SEQUENCE: 3
gcaaattcca tggcaccgt                                                    19

<210> SEQ ID NO 4
<211> LENGTH: 18
<212> TYPE: DNA
<213> ORGANISM: Artificial Sequence
<220> FEATURE:
<223> OTHER INFORMATION: Synthesized DNA fragment of reverse primer for
      GAPDH

<400> SEQUENCE: 4
tcgccccact gattttgg                                                     18

<210> SEQ ID NO 5
<211> LENGTH: 20
<212> TYPE: DNA
<213> ORGANISM: Artificial Sequence
<220> FEATURE:
<223> OTHER INFORMATION: Synthesized DNA fragment of forward primer for
      interleukin-10 (IL-10)

<400> SEQUENCE: 5
gcctaacatg cttcgagatc                                                   20

<210> SEQ ID NO 6
<211> LENGTH: 20
<212> TYPE: DNA
<213> ORGANISM: Artificial Sequence
<220> FEATURE:
<223> OTHER INFORMATION: Synthesized DNA fragment of reverse primer for
      IL-10

<400> SEQUENCE: 6
tgatgtctgg gtcttggttc                                                   20

<210> SEQ ID NO 7
<211> LENGTH: 20
<212> TYPE: DNA
<213> ORGANISM: Artificial Sequence
<220> FEATURE:
<223> OTHER INFORMATION: Synthesized DNA fragment of forward primer for
      transforming growth factor beta

<400> SEQUENCE: 7
aaatggatac acgaacccaa                                                   20

<210> SEQ ID NO 8
<211> LENGTH: 21
<212> TYPE: DNA
<213> ORGANISM: Artificial Sequence
<220> FEATURE:
<223> OTHER INFORMATION: Synthesized DNA fragment of reverse primer for
      transforming growth factor beta

<400> SEQUENCE: 8
gctgcatttg caagacttta c                                                 21

```
<210> SEQ ID NO 9
<211> LENGTH: 19
<212> TYPE: DNA
<213> ORGANISM: Artificial Sequence
<220> FEATURE:
<223> OTHER INFORMATION: Synthesized DNA fragment of forward primer for
      glyceraldehyde-3-phosphate dehydrogenase (GAPDH)

<400> SEQUENCE: 9
gcaaattcca tggcaccgt                                               19

<210> SEQ ID NO 10
<211> LENGTH: 18
<212> TYPE: DNA
<213> ORGANISM: Artificial Sequence
<220> FEATURE:
<223> OTHER INFORMATION: Synthesized DNA fragment of reverse primer for
      GAPDH

<400> SEQUENCE: 10
tcgccccact gattttgg                                                18

<210> SEQ ID NO 11
<211> LENGTH: 23
<212> TYPE: DNA
<213> ORGANISM: Artificial Sequence
<220> FEATURE:
<223> OTHER INFORMATION: Synthesized DNA fragment of forward primer for
      tumor necrosis factor-alpha

<400> SEQUENCE: 11
ccaggcagtc agatcatctt ctc                                          23

<210> SEQ ID NO 12
<211> LENGTH: 23
<212> TYPE: DNA
<213> ORGANISM: Artificial Sequence
<220> FEATURE:
<223> OTHER INFORMATION: Synthesized DNA fragment of reverse primer for
      tumor necrosis factor-alpha

<400> SEQUENCE: 12
agctggttat ctctcagctc cac                                          23

<210> SEQ ID NO 13
<211> LENGTH: 20
<212> TYPE: DNA
<213> ORGANISM: Artificial Sequence
<220> FEATURE:
<223> OTHER INFORMATION: Synthesized DNA fragment of forward primer for
      beta-actin

<400> SEQUENCE: 13
gtgggccgcc ctaggcacca                                              20

<210> SEQ ID NO 14
<211> LENGTH: 20
<212> TYPE: DNA
<213> ORGANISM: Artificial Sequence
<220> FEATURE:
<223> OTHER INFORMATION: Synthesized DNA fragment of reverse primer for
      beta-actin

<400> SEQUENCE: 14
tggccttagg gttcaggggg                                              20
```